United States Patent
Sano et al.

(10) Patent No.: US 8,408,063 B2
(45) Date of Patent: Apr. 2, 2013

(54) ULTRASONIC PROBE, AND ULTRASONIC DIAGNOSTIC APPARATUS USING THE SAME

(75) Inventors: Shuzo Sano, Tokyo (JP); Makoto Fukada, Tokyo (JP); Akifumi Sako, Tokyo (JP)

(73) Assignee: Hitachi Medical Corporation, Tokyo (JP)

( * ) Notice: Subject to any disclaimer, the term of this patent is extended or adjusted under 35 U.S.C. 154(b) by 268 days.

(21) Appl. No.: 12/744,020

(22) PCT Filed: Nov. 21, 2008

(86) PCT No.: PCT/JP2008/071239
§ 371 (c)(1), (2), (4) Date: May 20, 2010

(87) PCT Pub. No.: WO2009/069555
PCT Pub. Date: Jun. 4, 2009

(65) Prior Publication Data
US 2010/0242612 A1  Sep. 30, 2010

(30) Foreign Application Priority Data
Nov. 29, 2007 (JP) ................................. 2007-308118

(51) Int. Cl.
*G01N 29/00* (2006.01)
(52) U.S. Cl. .......................................... 73/632; 73/633
(58) Field of Classification Search ............ 73/632, 73/633; 310/327, 334, 335
See application file for complete search history.

(56) References Cited

U.S. PATENT DOCUMENTS

| | | | | |
|---|---|---|---|---|
| 4,385,255 | A * | 5/1983 | Yamaguchi et al. | 310/335 |
| 4,571,520 | A * | 2/1986 | Saito et al. | 310/327 |
| 4,786,017 | A * | 11/1988 | Wegerhoff et al. | 244/171.7 |
| 5,894,452 | A | 4/1999 | Ladabaum | |
| 6,714,484 | B2 | 3/2004 | Ladabaum | |
| 6,787,974 | B2 * | 9/2004 | Fjield et al. | 310/335 |
| 7,470,232 | B2 * | 12/2008 | Hoctor et al. | 600/453 |
| 7,545,075 | B2 * | 6/2009 | Huang et al. | 310/309 |
| 8,189,850 | B2 * | 5/2012 | Ono | 381/426 |
| 2005/0215909 | A1* | 9/2005 | Barnes | 600/459 |
| 2009/0082673 | A1* | 3/2009 | Lu et al. | 600/459 |

FOREIGN PATENT DOCUMENTS

| | | |
|---|---|---|
| JP | 62-115197 | 5/1987 |
| JP | 2001069594 | * 3/2001 |
| JP | 2007-201753 | 8/2007 |

* cited by examiner

*Primary Examiner* — J M Saint Surin
(74) *Attorney, Agent, or Firm* — Brundidge & Stanger, P.C.

(57) ABSTRACT

An ultrasonic probe including a cMUT chip that has plural oscillation elements whose electromechanical coupling coefficient or sensitivity varies in accordance with a bias voltage and transmits/receives an ultrasonic wave, an acoustic lens provided at an ultrasonic wave transmission/reception side of the cMUT chip, a backing layer provided to the opposite surface of the cMUT chip to the acoustic lens, and a substrate provided between the backing layer and the cMUT chip. The ultrasonic probe further includes thermal stress suppressing means for suppressing thermal stress occurring due to the difference in linear expansion coefficient caused by temperature variation between the substrate and the backing layer.

8 Claims, 6 Drawing Sheets

ULTRASONIC PROBE, AND ULTRASONIC DIAGNOSTIC APPARATUS USING THE SAME

TECHNICAL FIELD

The present invention relates to an ultrasonic probe using cMUT (Capacitive Micromachined Ultrasonic Transducer) chip, and particularly to a technique for securing long-term reliability of an ultrasonic probe.

BACKGROUND ART

An ultrasonic diagnostic apparatus is an apparatus for picking up a diagnosis image on the basis of an echo signal output from an ultrasonic probe and a reflection signal thereof. Plural ultrasonic oscillators are arranged in the ultrasonic probe. The ultrasonic oscillator converts a driving signal to an ultrasonic wave and transmits the ultrasonic wave to an examinee, and also it receives a reflection echo signal generated from the examinee and converts the reflection echo signal into an electrical signal.

A broad-band ultrasonic probe using cMUT chip has been recently developed. The cMUT chip is a hyperfine capacitance type ultrasonic oscillator manufactured by a semiconductor microfabrication process (for example, Patent Document 1).

In an example of the structure of a backing layer of this type of ultrasonic probe, the acoustic impedances of the backing layer and the cMUT chip are matched with each other in order to suppress unnecessary vibration of an electrode at the backing layer side in the cMUT chip (for example, Patent Document 2).

Patent Document 1: U.S. Pat. No. 5,894,452
Patent Document 2: U.S. Pat. No. 6,714,484

DISCLOSURE OF THE INVENTION

Problem to be Solved by the Invention

However, with respect to the ultrasonic probe using the cMUT chip, when there is some difference in linear expansion coefficient between the cMUT chip formed of silicon wafer and a backing material, thermal stress is mutually applied to each other due to temperature variation, and thus exfoliation or the like occurs between the respective layers. Therefore, there has been an unsolved problem that long-term reliability is lost.

An object of the present invention is to provide an ultrasonic probe that can suppress an effect of thermal stress, and an ultrasonic diagnostic apparatus using the ultrasonic probe.

Means of Solving the Problem

An ultrasonic probe of the present invention has the following constituent elements.

(1) An ultrasonic probe including a cMUT chip that has plural oscillation elements whose electromechanical coupling coefficient or sensitivity varies in accordance with a bias voltage and transmits/receives an ultrasonic wave, an acoustic lens provided at an ultrasonic wave transmission/reception side of the cMUT chip, a backing layer provided to the opposite surface of the cMUT chip to the acoustic lens, and a substrate provided between the backing layer and the cMUT chip is characterized by further comprising thermal stress suppressing means for suppressing thermal stress occurring due to the difference in linear expansion coefficient caused by temperature variation between the substrate and the backing layer.

(2) The thermal stress suppressing means may be formed of a material which makes the backing layer and the cMUT chip substantially coincident with each other in linear expansion coefficient.

(3) The thermal stress suppressing means may be formed of a third material having a linear expansion coefficient different from those of metal and resin constituting the backing layer.

(4) The third material may be a material containing silicon dioxide as a main component.

(5) The third material may be a fibrous material containing silicon dioxide as a main component.

(6) The metal may be tungsten, and the fiber may be polyamide resin.

(7) The linear expansion coefficient of the backing layer may be 50 to 60 ppm/° C. with respect to the linear expansion coefficient of the semiconductor substrate.

(8) The thermal stress suppressing means may be provided with an adjusting layer for adjusting the difference of the linear expansion coefficient between the cMUT chip and the backing layer.

(9) The adjusting layer may be formed of a material having a smaller modulus of elasticity than the cMUT chip and/or the backing layer.

(10) The adjusting layer may be an adhesive layer for fixing the cMUT chip to the backing layer, and formed of a material having a smaller modulus of elasticity than the cMUT chip and/or the backing layer.

(11) The adhesive layer may be formed of adhesive agent of epoxy type adhesive agent, polyurethane type adhesive agent or silicon type adhesive agent.

(12) The adjusting layer may be formed of a material that has rubber elasticity when hardened and has adhesiveness to materials at the interface.

An ultrasonic diagnostic apparatus according to the present invention comprises: an ultrasonic probe for transmitting/receiving an ultrasonic wave to an examinee; an image processor for constituting an ultrasonic image on the basis of an ultrasonic reception signal output from the ultrasonic probe; and a display unit for displaying the ultrasonic image, wherein the ultrasonic probe is an ultrasonic probe described in any one of the foregoing (1) to (12).

Effect of the Invention

According to the present invention, there can be provided the ultrasonic probe which can suppress the effect of the thermal stress, and the ultrasonic diagnostic apparatus using the ultrasonic probe.

Figure 1:
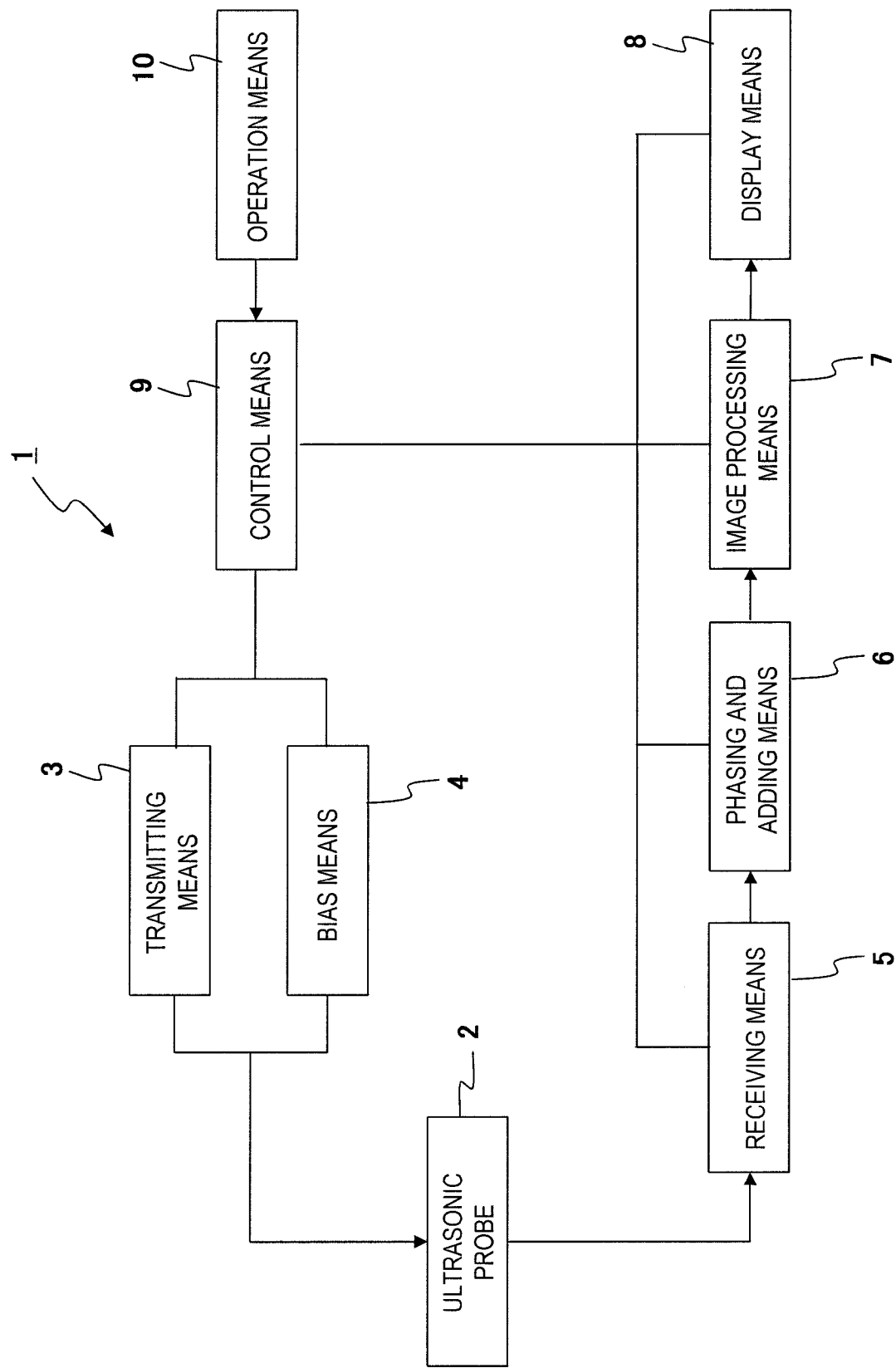
FIG. 1 is a diagram showing an example of the construction of an ultrasonic diagnostic apparatus according to an embodiment of the present invention.

DESCRIPTION OF REFERENCE NUMERALS 20 cMUT chip, 22 backing layer, 25 ultrasonic probe cover, 26 acoustic lens, 70, 71 adhesive layer, 72 flexible substrate, 86 wire, 87 wire sealing resin, 90 adhesive layer

BEST MODE FOR CARRYING OUT INVENTION

A preferred embodiment of an ultrasonic diagnosis probe according to the present invention and an ultrasonic diagnostic apparatus using the ultrasonic probe will be described in detail with reference to the accompanying drawings. In the following description and the accompanying drawings, the constituent elements having substantially the same function are represented by the same reference numerals, and the duplicative description thereof is omitted.

First, the construction of the ultrasonic diagnostic apparatus 1 will be described with reference to FIG. 1.

FIG. 1 is a diagram showing the construction of the ultrasonic diagnostic apparatus 1.

The ultrasonic diagnostic apparatus 1 according to the present invention includes an ultrasonic probe 2, transmitting means 3, bias means 4, receiving means 5, phasing adding means 6, image processing means 7, display means 8, control means 9 and operating means 10.

The ultrasonic probe 2 is brought into contact with an examinee to transmit/receive an ultrasonic wave to/from the examinee. An ultrasonic wave is emitted from the ultrasonic probe 2 to the examinee, and a reflection echo signal generated from the examinee is received by the ultrasonic probe 2.

The transmitting means 3 and the bias means 4 apply a bias voltage to electrodes which are disposed in the ultrasonic probe 2 so as to confront each other, and also apply a driving signal while superposed on the bias voltage, thereby emitting an ultrasonic wave.

The receiving means 5 receives a reflection echo signal to the ultrasonic probe 2.

The receiving means 5 further performs processing such as analog-digital conversion, etc. on the received reflection echo signal.

The phasing adding means 6 is a device for phasing and adding the received reflection echo signal.

The image processing means 7 is a device for generating a diagnosis image (for example. tomogram or blood flow image) on the basis of the phased and added reflection echo signal.

The display means 8 is a display device for displaying the diagnosis image generated by the image processing means 7.

The control means 9 is a device for controlling the respective constituent elements described above.

The operating means 10 is a device for supplying the control means 9 with an instruction such as a sign for starting diagnosis or the like, for example. The operating means 10 is input equipment such as a track ball, a keyboard, a mouse or the like.

Next, the ultrasonic probe 2 will be described with reference to FIGS. 2 to 4.

Figure 2:
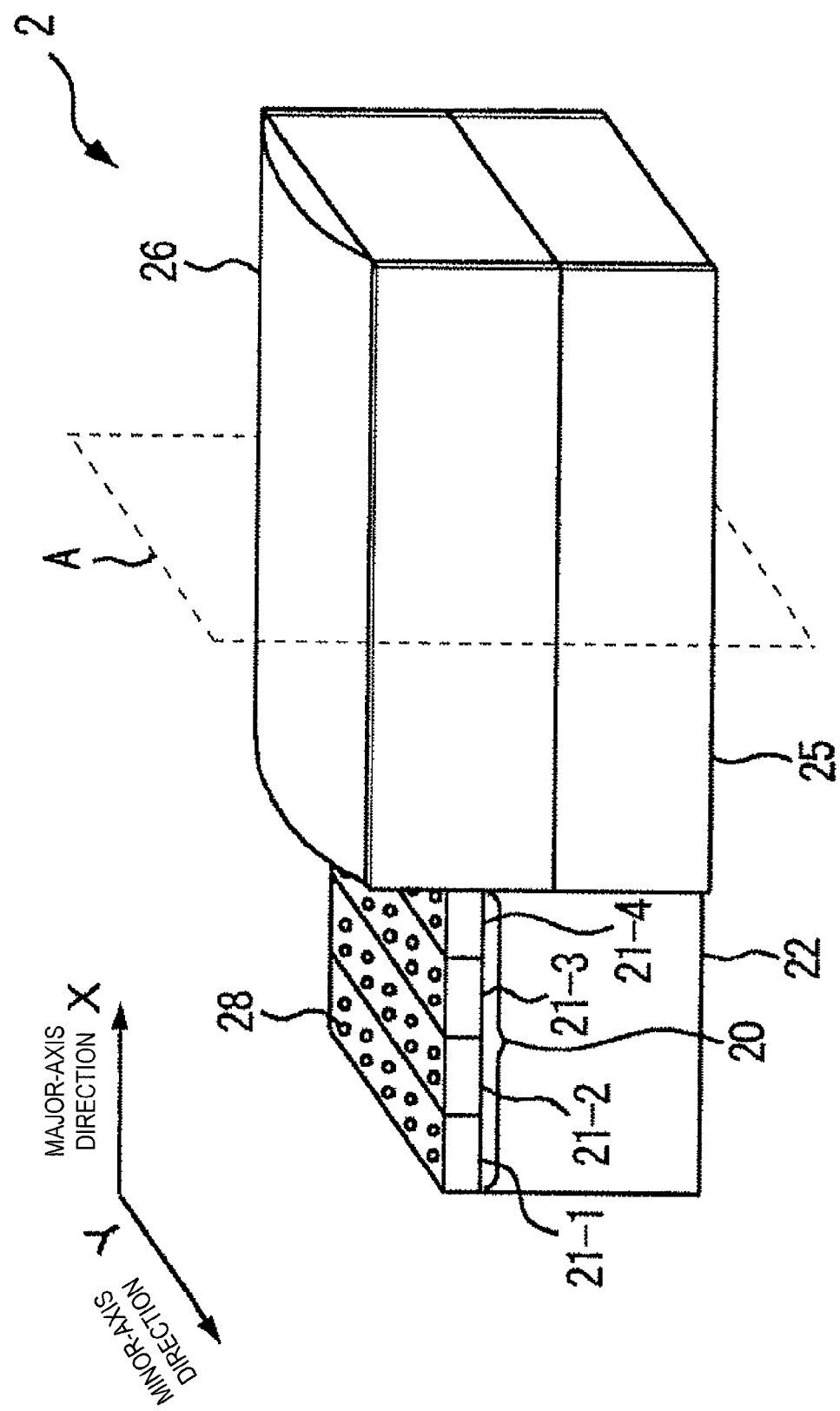
FIG. 2 is a perspective view of an ultrasonic probe adopted in FIG. 1.

FIG. 2 is a diagram showing the construction of the ultrasonic probe 2. FIG. 2 is a perspective view of the ultrasonic probe 2, and is a partially fractured view. The upper side of FIG. 2 is brought into contact with the examinee, and an ultrasonic wave is transmitted from the upper side.

The ultrasonic probe 2 has a cMUT chip 20. The cMUT chip 20 is a one-dimensional array type oscillator group in which plural oscillators 21-1, 21-2, . . . are arranged in a strip-shape. Plural oscillating elements 28 are arranged in the oscillators 21-1, 21-2, . . . . The ultrasonic probe 2 shown in FIG. 2 is a linear type probe, however, another type oscillator group such as a two-dimensional array type, a convex type or the like may be used.

A backing layer 22 is provided at the back surface side (the lower side in FIG. 2) of the cMUT chip 20. An acoustic lens 26 is provided at the ultrasonic wave emission side of the cMUT chip 20. The cMUT chip 20, the backing layer 22, etc. are stored in an ultrasonic probe cover 25.

In the cMUT chip 20, on the basis of application of a bias voltage of the bias means 4, a driving signal from the transmitting means 3 is converted to an ultrasonic wave, and the thus-converted ultrasonic wave is transmitted to an examinee.

The receiving means 5 converts an ultrasonic wave generated from the examinee to an electrical signal, and receives the ultrasonic wave as a reflection echo signal.

The backing layer 22 is a layer for absorbing propagation of an ultrasonic wave emitted from the cMUT chip 20 to the back surface side thereof to suppress surplus oscillation.

The acoustic lens 26 is a lens for converging an ultrasonic beam transmitted from the cMUT chip 20. The curvature of the acoustic lens 26 is determined on the basis of a desired focal length.

A matching layer may be provided between the acoustic lens 26 and the cMUT chip 20. The matching layer is a layer for matching the acoustic impedances of the cMUT chip 20 and the examinee to enhance the transmission efficiency of ultrasonic waves.

Figure 3:
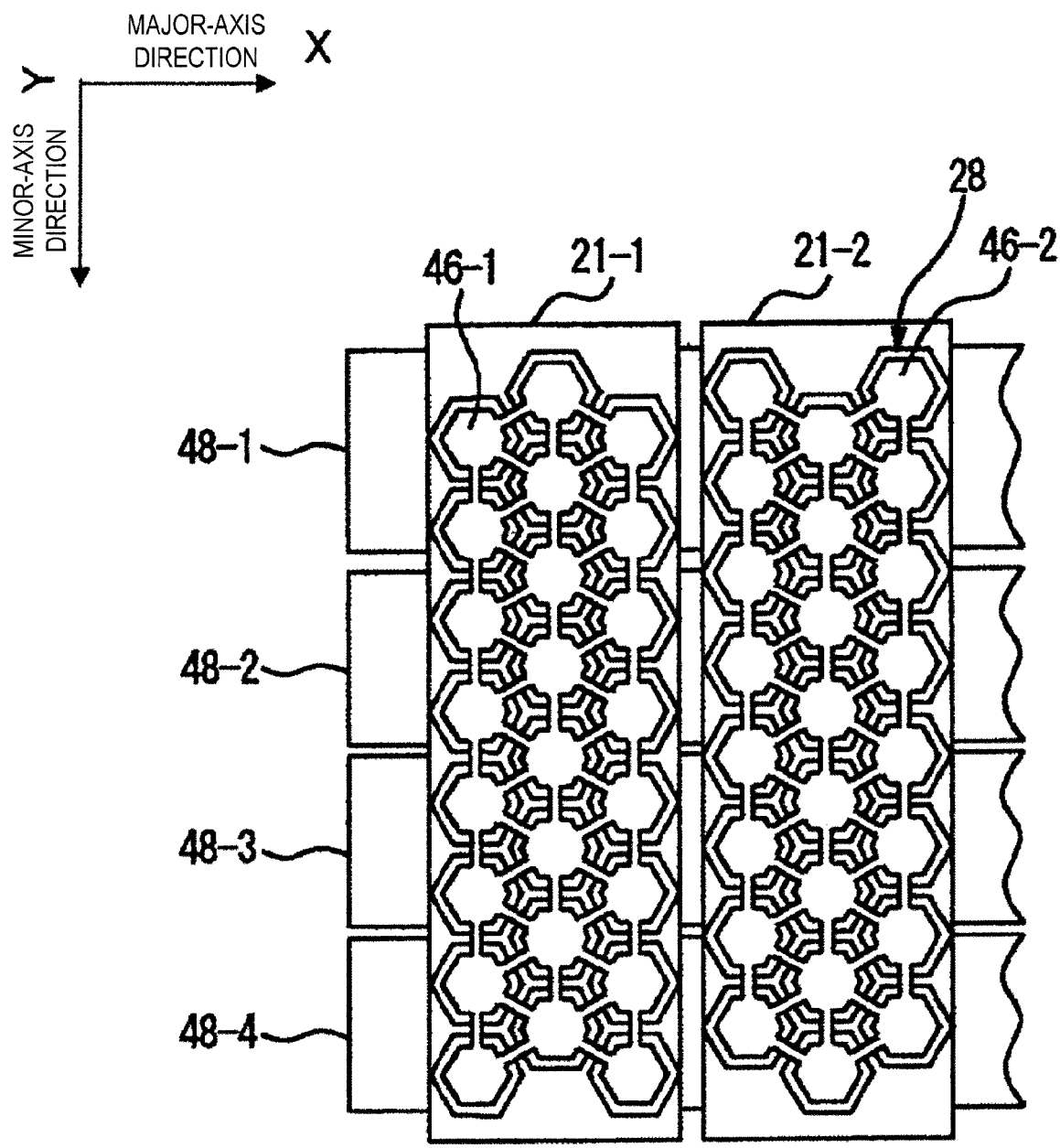
FIG. 3 is a diagram showing an example of the construction of an oscillator of FIG. 2.

FIG. 3 is a diagram showing the construction of the oscillators 21 of FIG. 2.

Upper electrodes 46-1, 46-2, . . . are arranged at the examinee side of the plural oscillating elements 28 constituting the oscillators 21-1, 21-2, . . . , and the upper electrodes are divided into plural parts in the longitudinal axis direction X and connected to one another every oscillator 21. That is, the upper electrode 46-1, the upper electrode 46-2, . . . are arranged in juxtaposition with one another in the longitudinal axis direction X.

Lower electrodes (48-1 to 48-4) are arranged at the opposite side of the plural oscillating elements 28 constituting the oscillators 21 to the examinee, and they are divided into plural parts (four lines in FIG. 3) in the short axis direction Y and connected to one another. That is, the lower electrode 48-1, the lower electrode 48-2, the lower electrode 48-3, . . . are arranged in juxtaposition with one another in the short axis direction Y.

Figure 4:
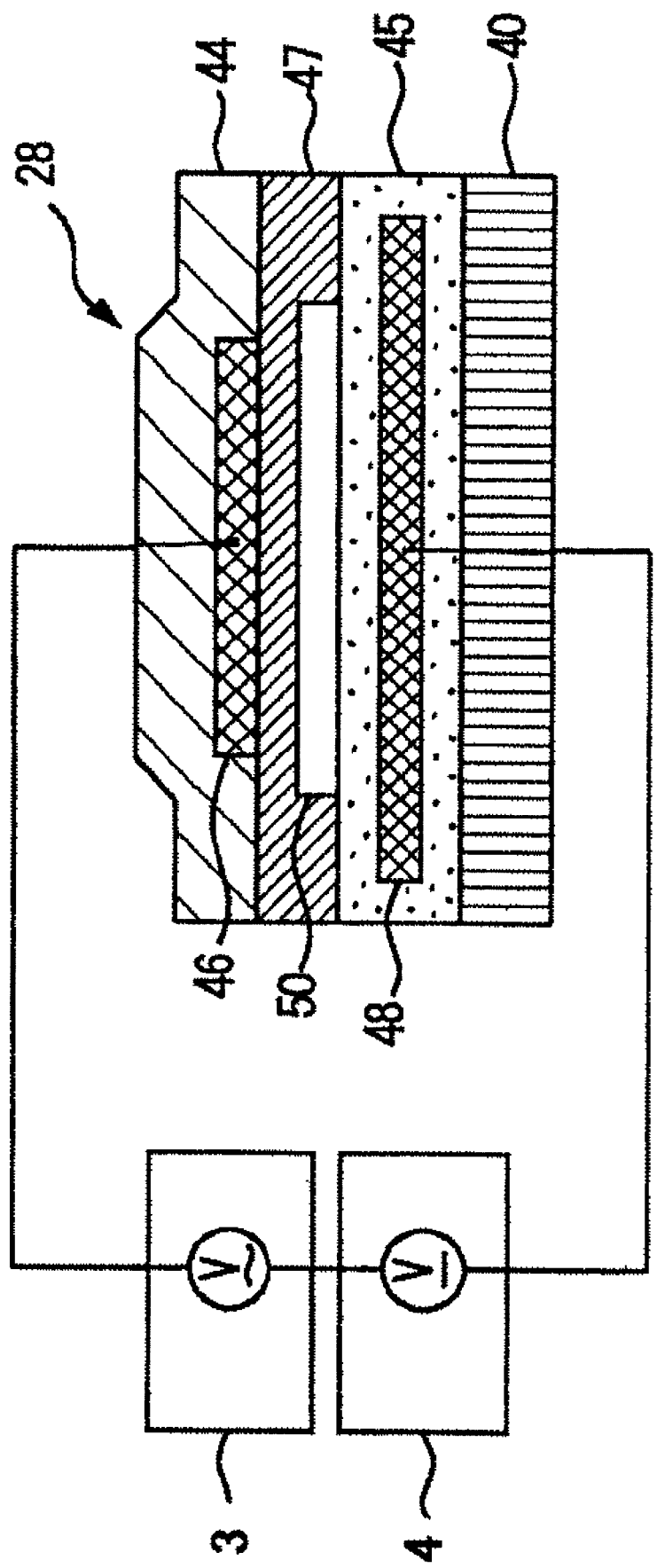
FIG. 4 is a cross-sectional view taken when one of oscillating elements of FIG. 3 is viewed from the side surface.

FIG. 4 is a side view (cross-sectional view) showing the construction of one of the oscillating elements 28 of FIG. 3.

The oscillating element 28 comprises a substrate 40, a film body 44, a film body 45, an upper electrode 46, a frame body 47 and a lower electrode 48. The oscillating element 28 is formed by microfabrication based on a semiconductor process. The oscillating element 28 corresponds to one element of cMUT.

The substrate 40 is a semiconductor substrate such as silicon wafer or the like, and disposed at the lower electrode side.

The film body 44 and the frame body 47 are formed of a semiconductor compound such as silicon compound or the like. The film body 44 is provided so as to be nearest to the examinee side (ultrasonic wave emission side) in the oscillating element 28, and the frame body 47 is disposed on the back surface (the opposite side to the examinee side) of the film body 44. The upper electrode 46 is provided between the film body 44 and the frame body 47. The film body 45 is provided between the frame body 47 and the substrate 40, and the lower electrode 48 is provided in the film body 45. The internal space 50 compartmented by the frame body 47 and the film body 45 is set to a vacuum-state or filled with predetermined gas.

The upper electrode 46 and the lower electrode 48 are connected to the transmitting means 3 for supplying a AC high-frequency voltage as a driving signal and the bias means 4 for applying a DC voltage as a bias voltage.

When an ultrasonic wave is transmitted, a DC bias voltage (Va) is applied to the upper electrode 46 and the lower electrode 48 of the oscillating element 28, and electric field is generated by the bias voltage (Va). Tension occurs in the film body 44 due to the generated electric field, and it has a predetermined electromechanical coupling coefficient (Sa). When a driving signal is supplied from the transmitting means 3 to the upper electrode 46, an ultrasonic wave whose intensity is based on the electromechanical coupling coefficient (Sa) is emitted from the film body 44.

Furthermore, when another DC bias voltage (Vb) is applied to the upper electrode 46 and the lower electrode 48 of the oscillating element 28, electric field is generated by the bias voltage (Vb). Tension occurs in the film body 44 due to the generated electric field, and it has a predetermined electromechanical coupling coefficient (Sb). When a driving signal is supplied from the transmitting means 3 to the upper electrode 46, an ultrasonic wave whose intensity is based on the electromechanical coupling coefficient (Sb) is emitted from the film body 44.

Here, when the bias voltage satisfies "Va<Vb", the electromechanical coupling coefficient satisfies "Sa<Sb".

On the other hand, when an ultrasonic wave is received, the film body 44 is excited by a reflection echo signal generated from the examinee, and the capacitance of the internal space 50 varies. The variation amount of the internal space 50 is detected as an electrical signal through the upper electrode 46.

The electromechanical coupling coefficient of the oscillating element 28 is determined by tension loaded on the film body 44. Accordingly, the tension of the film body 44 is controlled by changing the magnitude of the bias voltage applied to the oscillating element 28, whereby the intensity (or sound pressure, amplitude) of the ultrasonic wave emitted from the oscillating element 28 can be varied even when a driving signal having the same amplitude is input.

Next, an example 1 of the present invention will be described with reference to FIGS. 5 and 6.

Figure 5:
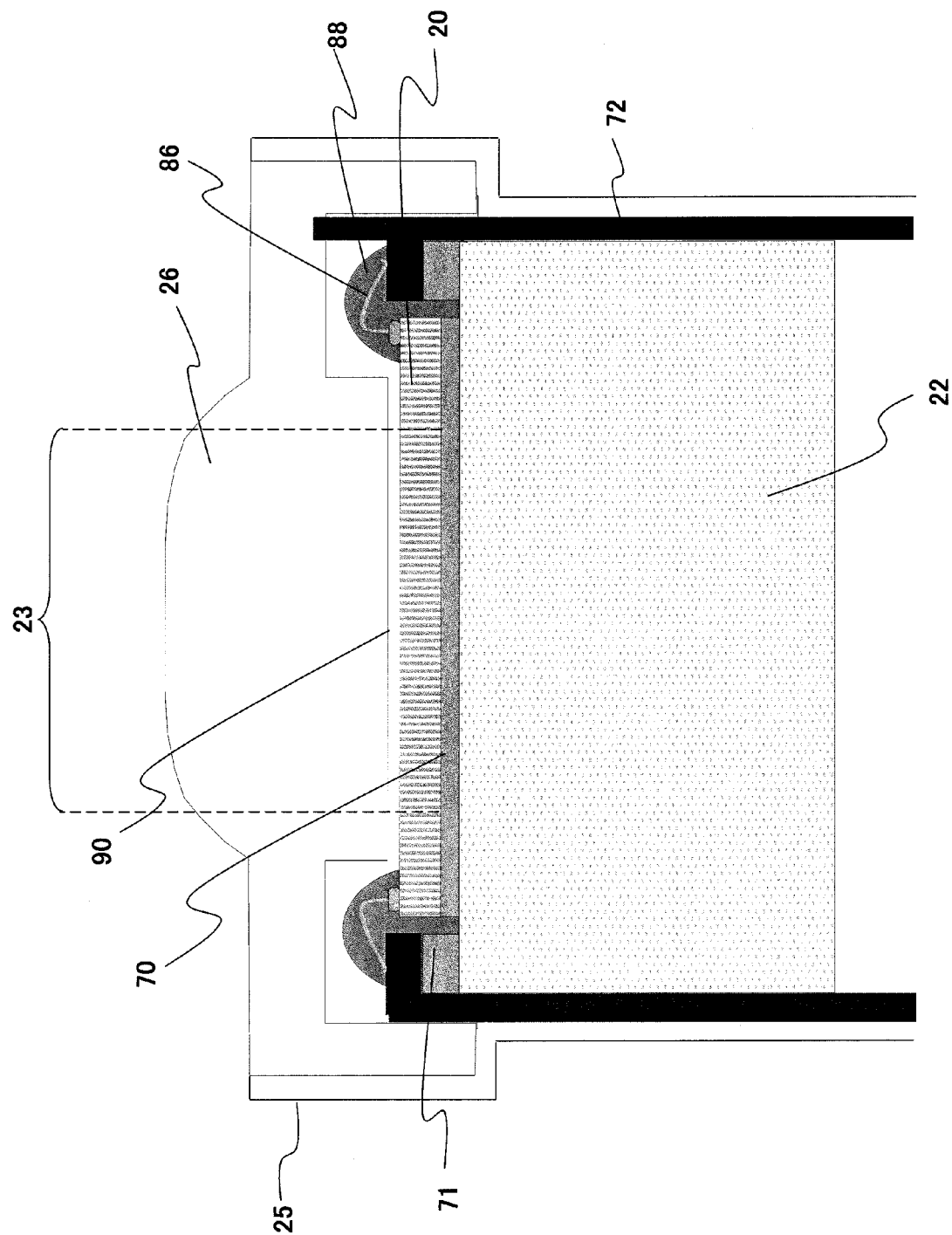
FIG. 5 is a diagram showing an ultrasonic probe according to an example 1.

FIG. 5 is a diagram showing an ultrasonic probe 2 according to an example 1. FIG. 5 is a cross-sectional view of a plan A of the ultrasonic probe of FIG. 2.

According to FIG. 5, the back surface of the acoustic lens 26 (the opposite side to the examinee disposing side, the backing layer side) has a recess portion so that the cMUT chip 20 is disposed in the recess portion. The connection portion (wire preventing resin 88) between the cMUT chip 20 and a flexible substrate 72 is fitted in the recess portion.

The cMUT chip 20 is mounted on the upper surface of the backing layer 22 through an adhesive layer 70. The flexible substrate 72 (Flexible Printed Circuits: FPC) is provided so as to extend from the peripheral edge of the upper surface of the backing layer 22 to the four side surfaces. The flexible substrate 72 is mounted on the peripheral edge of the upper surface of the backing layer 22 through an adhesive layer 71.

The adhesive layer 70 and the adhesive layer 71 are adhesive agent formed of epoxy resin, for example. The position in the height direction of the cMUT chip 20 and the flexible substrate 72 can be adjusted by arbitrarily adjusting the layer thickness of the adhesive layer 70 and the adhesive layer 71.

The flexible substrate 72 and the cMUT chip 20 are electrically connected to each other through a wire 86. The wire 86 is connected by a wire bonding method. An Au wire or the like may be used as the wire 86. Wire sealing resin 88 is filled around the wire 86.

The acoustic lens 26 is mounted on the upper surface of the cMUT chip 20 through an adhesive layer 90. Silicon rubber is used as a material of the acoustic lens 26, for example. With respect to the material of the adhesive layer 90, the same material as the acoustic lens 26 (for example, silicon) is desired.

The upper surface of the acoustic lens 26 is designed in a convex shape within at least an area 23 which corresponds to an area where an ultrasonic wave is emitted. The oscillating element 28 is disposed within the range corresponding to at least the area 23. An ultrasonic wave is emitted from the convex portion at the ultrasonic wave emission side (the examinee side) of the acoustic lens 26.

The ultrasonic probe cover 25 is provided to the four side surfaces of the ultrasonic probe 2. The ultrasonic probe cover 25 is fixed to the four side surfaces of the acoustic lens 26. An examiner manipulates the ultrasonic probe 2 while gripping the ultrasonic probe cover 25 by his/her hand.

Figure 6:
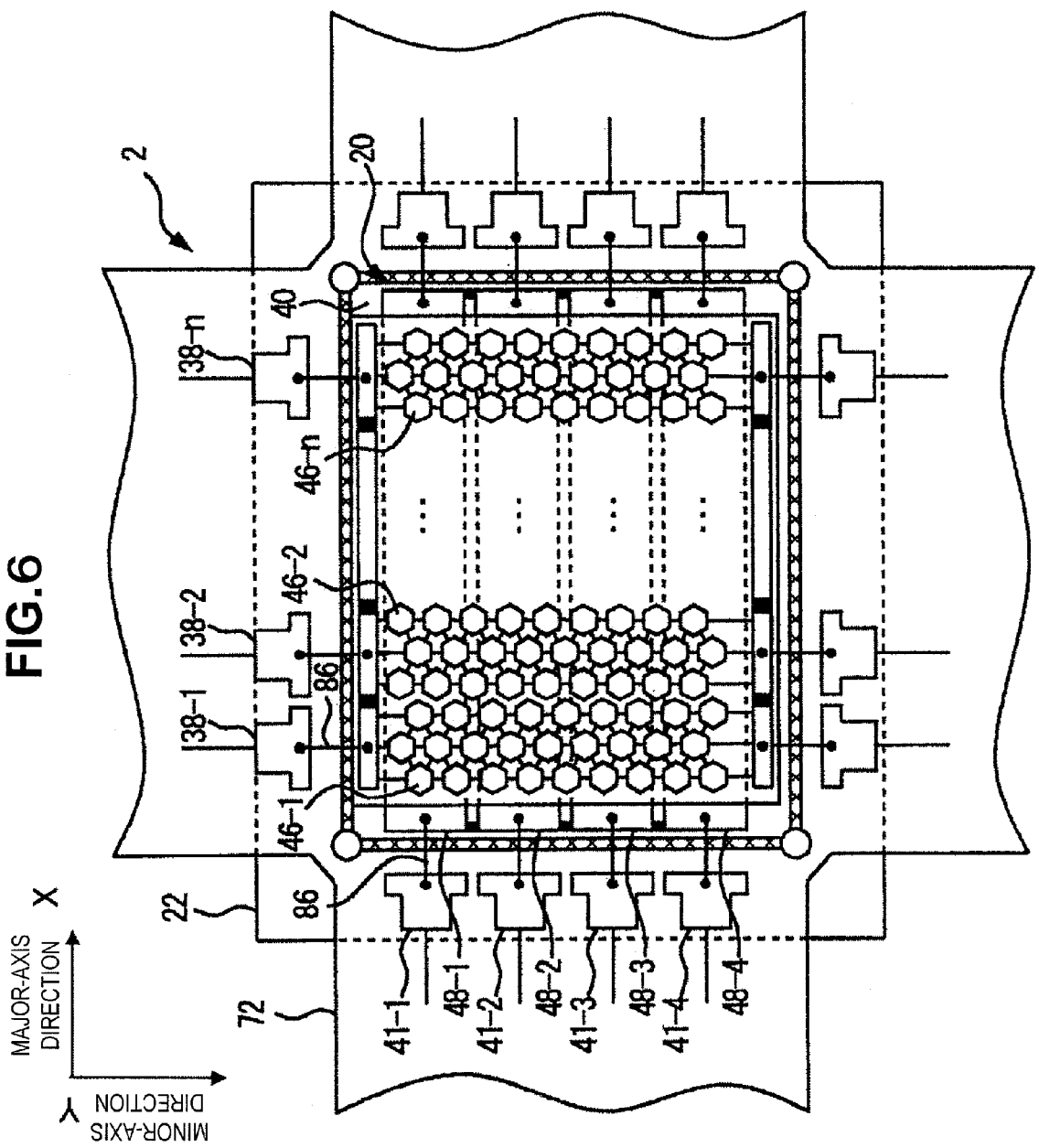
FIG. 6 is a diagram showing wires of the ultrasonic probe 2.

FIG. 6 is a diagram showing the wires of the ultrasonic probe 2.

The substrate 40 of the cMUT chip 20 is fixed to the upper surface of the backing layer 22. The flexible substrate 72 is fixed to the peripheral edge of the upper surface of the backing layer 22.

On the flexible substrate 72 are disposed signal patterns 38-1 to signal patterns 38-$n$ which are respectively paired at the upper and lower sides on the paper surface, and signal patterns 41-1 to signal patterns 41-4 which are respectively paired at the right and left sides on the paper surface.

The upper electrode 46-1 to the upper electrode 46-$n$ are connected to the signal pattern 38-1 to the signal pattern 38-$n$. The lower electrode 48-1 to the lower electrode 48-4 are connected to the signal pattern 41-1 to the signal pattern 41-4. The adjacent lower electrodes 48-1 to 48-4 are respectively insulated from one another.

The upper electrodes 46 and the lower electrodes 48 are respectively connected to the flexible substrate 72 through wires 86 by the wire bonding method.

The shape of the lower electrodes 48-1 to 48-4 is desirably set to the shape (for example, wave form) corresponding to the shape of the oscillating element 28 (for example, hexagonal shape), whereby each oscillating element 28 can be disposed so as to correspond to only one of the lower common electrodes 48-1 to 48-4.

Furthermore, the four lower electrodes 48-1 to 48-4 are disposed, however, the number of the lower electrodes is not limited to this value.

The signal patterns 38-1 to 38-$n$ are provided so as to be paired at both the upper and lower sides on the paper surface, and the signal patterns 48-1 to 48-4 are provided so as to be paired at both the right and left sides on the paper surface. However, the present invention is not limited to this arrangement, and they may be provided at only one side without being paired.

The signal pattern and the upper electrode or the lower electrode are connected to each other by the wire bonding method. However, the present invention is not limited to this method, and a flip chip bonding method for connecting them through pads may be used.

Example 1

First, an example 1 of the present invention will be described.

In this example, the backing layer 22 which absorbs propagation of ultrasonic waves emitted from the cMUT chip 20 to the back surface side to suppress surplus oscillation has the following feature.

First, with respect to the backing layer according to this example, the linear expansion coefficient thereof is set to a low value so that it approaches to that of the substrate 40 (silicon wafer) of the cMUT chip 20.

When there is some difference in linear expansion coefficient between the substrate 40 (for example, silicon wafer) of the cMUT chip 20 and the backing layer, there has been hitherto a problem in long-term reliability of the probe because unnecessary friction or force is applied to the contact surface every time temperature rises and thus the contact surface is worn. For example, silicon wafer has a linear expansion coefficient of about 3 ppm/° C., and the conventional backing layer is formed of materials such as metal and resin and thus has a linear expansion coefficient of 100 ppm/° C. order. However, with respect to the backing layer according to this example, the linear expansion coefficient thereof is set to 50 ppm/° C., for example. Therefore, the long-term reliability problem of the probe which is caused by the application of unnecessary friction or force to the contact surface every increase of temperature and thus wearing of the contact surface can be solved.

More specifically, a new material for reducing the linear expansion coefficient of the backing layer is mixed in the backing layer as thermal effect reducing means for reducing a thermal effect caused by the difference in linear expansion coefficient between the backing layer an the substrate of the cMUT chip. The new material is a third material different from the metal (for example, tungsten, ferrite, Pt, ceramic fine particle, etc.) and the resin (for example, polyamide resin, epoxy resin, copolymer of vinyl chloride and vinyl acetate, rubber, etc.) which constitute the backing layer. The third material is formed of glass-like material containing silica ($SiO_2$) as a main component, and it may be glass fiber or the like, for example. The new material has a linear expansion coefficient of about 0.5 ppm/° C. (in the case of quartz glass) or about 9 ppm/° C. (in the case of general glass), and thus the linear expansion coefficient of the backing layer can be reduced as a whole. The linear expansion coefficient of the backing layer is near to 50 to 60 ppm/° C. as a whole with respect to the linear expansion coefficient (3 ppm/° C.) of the substrate (for example, silicon wafer) of the cMUT chip 20. The difference in linear expansion coefficient between the backing layer and the substrate of the cMUT chip may be set within the difference range of 50 to 60 ppm/° C., and more preferably the linear expansion coefficient is coincident therebetween.

The backing material according to this example contains tungsten particles (W particle), polyamide resin and glass fiber.

In the above example, the difference in linear expansion coefficient between the substrate of the cMUT chip 20, for example, silicon wafer and the backing layer is reduced, and the situation that unnecessary friction or force is applied to the contact surface every increase of temperature and thus the contact surface is worn is suppressed, and thus the long-term reliability of the probe can be secured.

By forming the backing layer of the material as described above, the acoustic impedance of the backing material itself is equal to 7 to 20 MRayl, and it is not necessarily coincident with the impedance of the substrate of the cMUT chip (for example, 20 MRayl), however, this does not greatly affect the acoustic characteristic from an experiment result obtained by the inventor. According to the structure of this example, it is not necessarily required that a material having an intermediate linear expansion coefficient is installed between the cMUT chip and the backing material, and thus there is an advantage that the manufacturing can be easily performed.

Furthermore, in the backing layer disclosed in this invention, the thermal deformation temperature is equal to about 210° C. under 0.45 MPa, and thus thermal deformation hardly occurs even when thermal temperature increase occurs.

Example 2

Next, an example 2 of the present invention will be described.

Absorbing means for absorbing the difference in linear expansion coefficient between the cMUT chip and the backing layer is provided between the cMUT chip and the backing layer of this example as thermal effect reducing means for reducing a thermal effect caused by the difference in linear expansion coefficient between the backing layer and the cMUT chip substrate. The absorbing means is formed of a material having a small elasticity modulus.

In this example, the adhesive agent for bonding the cMUT chip and the backing layer is formed of a material having small elasticity modulus. Since the adhesive agent having a small elasticity modulus is used, the difference in linear expansion coefficient between the cMUT chip and the backing layer can be absorbed. Therefore, the situation that unnecessary friction or force is applied to the contact surface every increase of temperature and thus the contact surface is worn is suppressed, and thus an ultrasonic probe having long-term reliability can be provided.

More specifically, the absorbing means according to this example has a smaller elasticity modulus as compared with any one or both of the substrate constituting the cMUT chip and the backing layer. For example, a material which has rubber elasticity (for example, elongation percentage of 100% or more) when it is hardened and has adhesiveness to materials at the interface may be considered as the material constituting the absorbing means. When the material constituting the absorbing means is adhesive agent, epoxy resin type adhesive agent, polyurethane type adhesive agent, silicon type adhesive agent or the like which has low elasticity is considered.

According to the above example, with respect to the ultrasonic probe using the cMUT chip and the ultrasonic diagnostic apparatus using the ultrasonic probe, the structure of the backing layer for absorbing the propagation of ultrasonic waves emitted from the back surface side of the cMUT chip can suppress the effect of the thermal stress.

The preferred embodiment of the medical image display device according to the present invention has been described, however, the present invention is not limited to the above embodiment. It is apparent that persons skilled in the art can make various modifications or alterations within the scope of the technical idea disclosed in this application, and it is necessarily understood that these modifications and alterations belong to the technical compass of this invention.

The invention claimed is:

1. An ultrasonic probe including:
   a cMUT (Capacitive Micromachined Ultrasonic Transducer) chip that has plural oscillation elements whose electromechanical coupling coefficient or sensitivity varies in accordance with a bias voltage and transmits/receives an ultrasonic wave;
   an acoustic lens provided at an ultrasonic wave transmission/reception side of the cMUT chip; and a backing layer provided to the opposite surface of the cMUT chip to the acoustic lens,
wherein the cMUT chip has a substrate made of a silicon wafer, the substrate being joined through an adhesive layer with the backing layer that comprises a material including silicon dioxide.

2. The ultrasonic probe according to claim 1, wherein the backing layer further comprises a metal and a resin, both the metal and the resin having linear expansion coefficients that are different from the linear expansion coefficient of the material.

3. The ultrasonic probe according to claim 2, wherein the metal is tungsten, and the resin is polyamide resin.

4. The ultrasonic probe according to claim 1, wherein the material is a fibrous material.

5. The ultrasonic probe according to claim 1, wherein the difference in the linear expansion coefficient between the backing layer and the substrate is in the range of 50 to 60 ppm/°C.

6. The ultrasonic probe according to claim 1, wherein an adhesive layer used for the adhesive layer has a modulus of elasticity smaller than the modulus of slasticity of the substrate and/or the backing layer.

7. The ultrasonic probe according to claim 6, wherein the adhesive agent is one of epoxy type, polyurethane type or silicon type.

8. An ultrasonic diagnostic apparatus comprising;
an ultrasonic probe for transmitting/receiving an ultrasonic wave to an examinee;
an image processor for constituting an ultrasonic image on the basis of an ultrasonic reception signal output from the ultrasonic probe; and
a display unit for displaying the ultrasonic image,
wherein the ultrasonic probe is an ultrasonic probe as described in any one of claims 1,2,4,5,6 and 7.

* * * * *